United States Patent [19]

Mitrani

[11] Patent Number: 5,753,612
[45] Date of Patent: May 19, 1998

[54] PHARMACEUTICAL COMPOSITION AND METHOD FOR INHIBITING HAIR GROWTH BY ADMINISTRATION OF ACTIVIN OR ACTIVIN AGONISTS

[75] Inventor: Eduardo Mitrani, Newton, Mass.

[73] Assignee: Yissum Research Development Co. of the Hebrew University of Jerusalem, Jerusalem, Israel

[21] Appl. No.: 385,185

[22] Filed: Feb. 7, 1995

Related U.S. Application Data

[63] Continuation-in-part of Ser. No. 967,262, Oct. 27, 1992, Pat. No. 5,387,262.
[51] Int. Cl.$^6$ .......................... A61K 38/17; C07K 14/47
[52] U.S. Cl. ........................ 514/2; 514/8; 514/12; 514/880; 514/887; 530/350
[58] Field of Search ..................... 530/350; 435/69.4; 514/2, 8, 12, 886, 887, 880

[56] References Cited

U.S. PATENT DOCUMENTS

| | | | |
|---|---|---|---|
| 4,798,885 | 1/1989 | Mason et al. | 530/350 |
| 5,037,643 | 8/1991 | Green | 424/70 |
| 5,223,409 | 6/1993 | Ladner et al. | 435/69.7 |
| 5,387,576 | 2/1995 | Mitrani | 514/2 |

FOREIGN PATENT DOCUMENTS

| | | |
|---|---|---|
| 0222491 | 10/1986 | European Pat. Off. |
| 0455422 | 4/1991 | European Pat. Off. |

OTHER PUBLICATIONS

Gallop et al. J. Med. Chem. 37(9):1233–1251, 1994
Feijen et al. Develop. 120:3621–3637, 1994.
Kretser and Robertson, Biol. Reprod. 40:33–47, 1989.
Jong et al. Adv. Exp Med Biol 274:271–293, 1990.
Bullough W.S. and Laurence E.B. "The control of epidermal mitotic activity in the mouse." *Proc. Roy. Soc. B.*, 151:517–536 (1959).
Bichel P. "Tumor growth inhibiting effect of JB–1 ascitic fluid –I" *Europ. J. Cancer* 6:291–296 (1970).
Rheinwald J. "Serial cultivation of normal human epidermal keratinocytes" In: *Methods in Cell Biology*, Academic Press, vol. 21A, pp. 229–254 (1980).
Mason A.J. et al. "Complementary DNA sequences of ovarian follicular fluid inhibin show precursor structure and homology with transforming growth factor–β." *Nature*, 318:659–663 (1985).
Ling N. et al. "Pituitary FSH is released by a heterodimer of the β–subunits from the two forms of inhibin." *Nature*, 321:779–782 (1986).
Yu J. et al. "Importance of FSH–releasing protein and inhibin in erythrodifferentiation." *Nature*, 330:765–767 (1987).
Eisinger M. et al. "Growth regulation of skin cells by epidermal cell–derived factors: Implications for wound healing." *Proc. Natl. Acad. Sci. USA*, 85:1937–1941 (1988).

Murata M. et al. "Erythroid differentiation factor is encoded by the same mRNA as that of the inhibin $\beta_A$ chain." *Proc. Natl. Acad. Sci. USA*, 85:2434–2438 (1988).
Thompson N.L. et al. "Expression of transforming growth factor–β1 in specific cells and tissues of adult and neonatal mice." *J. Cell Biol.*, 108:661–669 (1989).
Pelton R. W. et al. "Expressison of transforming growth factor β2 in RNA during murine embryogenesis." *Development*, 106:759–767 (1989).
Lyons K. et al. "Vgr–1, a mammalian gene related to Xenopus Vgr–1, is a member of the transforming growth factor β gene superfamily." *Proc. Natl. Acad. Sci. USA*, 86:4554–4558 (1989).
Choi Y. and Fuchs E. "TGF–β and retinoic acid: Regulators of growth and modifiers of differentiation in human epidermal cells." *Cell Regulation*, 1:791–809 (1990).
Albano R.M. et al. "A mesoderm–inducing factor produced by WEHI–3 murine myelomonocytic leukemia cells is activin A." *Development*, 110:435–443 (1990).
Schubert D. et al. "Activin is a nerve cell survival molecule." *Nature*, 344:868–870 (1990).
Smith J.C. et al. "Identification of a potent Xenopus mesoderm–inducing factor as a homologue of activin A." *Nature*, 345:729–731 (1990).
Asashima M. et al. "Mesodermal induction in early amphibian embryos by activin A (erythroid differentiation factor)." *Roux's Arch. Dev. Biol.*, 198:330–335 (1990).
Thomsen G. et al. "Activins are expressed early in Xenopus embryogenesis and can induce axial mesoderm and anterior structures." *Cell*, 63:485–493 (1990).
Mitrani E. and Shimoni Y. "Induction by soluble factors of arganized axial structures in chick epiblasts." *Science*, 247:1092–1094 (1990).
Dvir A. et al. "The inhibition of EGF–dependent proliferation of keratinocytes by tyrphostin tyrosine kinase blockers." *J. Cell Biol.*, 113:857–865 (1991).
Jones C.M. et al. "Involvement of bone morphogenetic protein–4 (BMP–4) and Vgr–1 in morphogenesis and neurogenesis in the mouse." *Development*, 111:531–542 (1991).
Matthews L.S. and Vale W.V. "Expression cloning of an activin receptor, a predicted transmembrane serine kinase." *Cell*, 65:973–982 (1991).
Blessing M. et al. "Transgenic mice as a model to study the role of TGF–β–related molecules in hair follicles." *Genes Dev.*, 7:204–215 (1993).

*Primary Examiner*—Vasu Jagannathan
*Assistant Examiner*—Christine Saoud
*Attorney, Agent, or Firm*—Foley, Hoag & Eliot LLP; Matthew P. Vincent; Beth E. Arnold

[57] ABSTRACT

Pharmaceutical preparations for controlling proliferation of ectodermally-derived tissues comprising the specific negative growth factor activin A or an agonist thereof, and their use in methods of treatment of proliferative conditions and wound repair.

15 Claims, 1 Drawing Sheet

FIGURE 1

PHARMACEUTICAL COMPOSITION AND METHOD FOR INHIBITING HAIR GROWTH BY ADMINISTRATION OF ACTIVIN OR ACTIVIN AGONISTS

RELATED APPLICATIONS

This application is a continuation-in-part of U.S. Ser. No. 07/967,262 filed Oct. 27, 1992, now U.S. Pat. No. 5,387,262, and entitled "Pharmaceutical Compositions Comprising Activin A", the teachings of which are incorporated herein by reference.

BACKGROUND OF THE INVENTION

Constant cell renewal in epithelial tissues is accomplished by a carefully balanced process in which new cells are constantly being produced in exact measure to the number of cells that are lost through cell death. Following wounding, a burst of mitotic activity takes place so that the number of cells produced outnumbers the cells that are dying. As the tissue mass is being replenished, mitotic activity slows so that eventually a new equilibrium between cell production and cell loss is obtained. Although it is clear that such process requires both positive and negative growth factors, the molecules involved in controlling epidermal homeostasis have not yet been characterized (Choi et al., *Cell Regulation*, 1: 791–809 (1990)). Transforming growth factors of the β type (TGFβs) are candidates to be major regulators in this process since it has been shown that both TGF-β1 and TGF-β2 can inhibit epidermal proliferation at ng/ml concentrations (Choi et al., supra). TGF-β1 messenger RNAs are expressed in terminally differentiating epidermal cells in vivo (Thomson et al., *J Cell. Biol.*, 108: 661–669 (1989)). Furthermore, TGF-β2 and the TGF-β-related gene, Vgr1, are expressed at the time that stratification and keratinization in developing mouse epidermis take place (Lyons et al., *Proc. Natl. Acad Sci. USA* 86: 4554–4558 (1989); Lyons et al., *Development* 106: 759–767 (1988). In spite of this it is not yet clear whether TGF-βs are major regulators of epidermal homeostasis. TGF-βs form part of a large family of molecules and although at first sight it appears that one factor can mimic the action of others, subtle differences often confer specificity and potentiation to different factors in different systems.

A feedback control is involved in epidermal homeostasis. Feedback control of epidermal cell proliferation is suggested by simple evidence. For example, under stress conditions the tissue never disappears although the mitotic activity is considerably depressed. Vice versa, psoriatic epidermis showing an abnormally high proliferative activity does not become thicker and thicker but reaches a homeostatic equilibrium.

This control is not due to contact inhibition. If keratinized or keratinizing cells are removed, for example by means of stripping with adhesive tape (Pinkus, H. J., *Invest. Dermatol.* 16: 383–386 (1951)) or by friction, the underlying basal cells respond by a burst of mitotic activity so that the cell loss is rapidly and locally compensated. It should be noted that even though the basal layer was not altered in this experiment there was a burst of mitotic activity suggesting that contact inhibition is unlikely to be involved in the growth control mechanism of normal epidermis. As in the case of a deeper wound, the enhanced cell proliferation was—apart from a period of overshooting—automatically reduced to its normal value when the repair had been finished.

From this it is obvious that experiments on wound healing and tissue repair can provide insight into the regulatory mechanisms governing epidermal cell proliferation, although the repair of skin lesions is a highly complex process including primarily epithelial cell migration as well as division of epidermal cells and a response of the underlying connective tissue.

In order to provoke the repair process, Bullough and Laurence (Bullough et al., *Proc. Roy. Soc. B.* 151: 517–536 (1960)), made a 1 cm long cut in the dorsal skin of mice which extended down through the panniculus carnosus. This resulted in a stimulation of mitotic activity which reached a peak after 36–48 h. This enhanced proliferative response was almost completely restricted to a zone with a width of 1 mm from the cut edge. Within this zone a gradient of mitotic activity with the highest activity proximal to the wound edge could be observed.

Feedback mitotic control in epidermis appears to be due to the presence of negative growth factors. In a second series of experiments said authors investigated the influence of a small cut made through the epidermis on one side of a mouse ear on the mitotic activity of the epidermis on the opposite side of the ear. A mouse ear is only about 0.15 mm thick and its two epidermal layers are separated by a very thin layer of connective tissue. It could be expected, therefore, that the zone of high mitotic activity adjacent to the wound would extend to the uninjured opposite side of the ear. Indeed, it was observed that the opposite undamaged epidermis showed a mitotic response which was as powerful as that adjacent to the wound. With proper control experiments, this effect was shown not to be due to the greatly enriched blood supply around the damaged area. The authors were thus left with the conclusion that the enhanced mitotic activity in the vicinity of the wound as well as on the opposite side of the ear was the consequence of either the production of a mitogenic agent (wound hormone, see Abercrombie, M., *Symposium Soc. Exp. Biol.* 11: 235 (1957)) or the loss of an endogenous inhibitor which is synthesized within the skin.

Bullough and Laurence (Bullough et al., *Proc. Roy. Soc. B.* 151: 517–536 (1960)) made a wound in the subcutaneous tissue including hair roots without damaging the overlying epidermis. Under these conditions no significant mitotic response of the epidermis was observed (though the wounded area developed a rich blood supply and suffered a heavy invasion of leucocytes). If the wound was not only a simple cut but a more extended lesion, the highest mitotic activity on the undamaged opposite side was found opposite to the center of the lesion. The authors considered this observation not to be consistent with the assumption of a wound hormone thought to be released from the wound edges but took it as strong evidence for the loss of a pre-existing mitotic inhibitor. They thus proposed that normally an inhibitory substance is in constant production, and that it may be lost partly with the cornified cells which are shed from the surface and partly by diffusion into the dermis. It may also be unstable. In the neighborhood of a wound there appears to be both a reduced inhibitor production and a drainage away of inhibitor into the wound (Bullough et al., *Proc. Roy. Soc. B.* 151: 517–536 (1960)). Iversen et al. (in *Virch. Arch. B.* 16: 157–159 (1974)) repeated and extended this type of experiment on wound healing in an impressive study using the web membrane of the African fruit bat. Since this tissue resembles a mouse ear in many aspects (the two epidermal layers are separated by a thin connective tissue sheet with a diameter of 1 mm or less) but is much larger and easier to handle, it was found to be an almost ideal object for the purpose envisaged.

When an area of epidermis was removed from the ventral side of the web by stripping with adhesive tape, several waves of increased mitotic activity and the development of epidermal hyperplasia were observed adjacent to the wound as well as on the central region of the undamaged opposite side. Furthermore, retransplantation of the epidermis to the stripped area (which in fact should have increased the sources of putative wound hormone) prevented development of hyperplasia opposite the wound.

Hyperproliferative Epidermal Conditions

There have been many studies attempting to describe and quantify the cell proliferation patterns of normal and diseased skin. Normal epidermis has a very low mitotic activity with cells cycling every 200–300 hours. Yet when the epidermis is wounded a burst of mitotic activity takes place so that the cells divide up to ten times faster depending on the conditions and the severity of the wound (Pinkus, H. J., Invest. Dermatol. 16: 383–386 (1951); Bullough et al., Proc. Roy. Soc. B. 151: 517–536 (1960)). In contrast, human hair root cells are rapidly proliferating cells with cell cycle times in the order of 35 hours. Whilst the data on psoriatic epidermis is more controversial there is general agreement that psoriasis is a disease characterized by epidermal cell hyperproliferation and incomplete keratinization (Weinstein et al., In: Psoriasis Cell Proliferation. Eds. Wright, N., Camplejohn, R. S. Churchill Livingstone (1983)). Estimation of cell cycle times for psoriasis vary from group to group and depend on the methods used. Weinstein et al. have conducted a study of normal and psoriatic epidermis in vivo using the frequency of labeled mitosis method and have reported that whilst the cell cycle time of normal skin is about 300 hours, involved psoriatic epidermal cells have a cell cycle time of about 37 hours (Weinstein et al., In: Psoriasis Cell Proliferation. Eds. Wright, N., Camplejohn, R. S. Churchill Livingstone (1983)).

The accessibility of cutaneous and genital epithelial tumors has permitted use of the fraction of labeled mitosis (FLM) method to study cell kinetics in these tissues. In basal cell carcinoma and in squamous cell carcinoma kinetic data have been obtained which show kinetic parameters comparable to those of hyperproliferative skin conditions. However, a second peak in the FLM curves (which would have given a direct estimation of the cell cycle times), has not been reported.

Members of the TGF-β Superfamily Induce Differentiation in Several Tissues

There is accumulating evidence that TGF-β related genes are important regulators of many morphogenetic events. TGF-β2 and β3 have been implicated in murine embryogenesis. Another group of the TGF-β family whose members show greatest homology to the drosophila gene DPP and the Xenopus gene Vg1 includes Bone Morphogenetic proteins (BMP) (Thomson et al., J Cell Biol., 108: 661–669 (1989); Lyons et al., Proc. Natl. Acad Sci. USA 86: 4554–4558 (1989)) (osteogenin), and 2b (now known as BMP-4) as well as the murine Vgr1, osteogenic protein 1, and GDF-1 (Jones et al., Development 111: 531–542 (1991)). Another subgroup of the TGF-β related molecules are the activins. The activins were initially found to elicit FSH release (Mason et al., Nature, 318: 659–663 (1985); Vale et al., Nature 321: 776–779 (1986); Ling et al., Nature 321: 779–782 (1986)). Two forms of activins have been isolated and shown to be either disulfide-linked homodimer of the inhibin βA subunit (activin-A) or a heterodimer composed of a βA and a βB subunit (activin AB) (Mason et al., Nature, 318: 659–663 (1985); Vale et al., Nature 321: 776–779 (1986); Ling et al., Nature 321: 779–782 (1986)). Activin A has also been found to stimulate erythroid differentiation (Yu. et al., Nature 330: 765–767 (1987)) and to promote neuron survival in vivo (Schubert et al., Nature 344: 868–870 (1990)). Activins, both A and B, have now been shown to induce the formation of mesodermal structures in Xenopus and chicks (Asashima et al., Roux's Arch. Dev. Biol. 198: 330–335 (1990); Smith et al., Nature 345: 729–731 (1990); Thomsen et al., Cell 63: 485–493 (1990); Mitrani et al., Science 247: 1092–1094 (1990); Mitrani et al., Cell 63: 495–501 (1990)).

Recently, the activins have been found to have strong differentiation capacities on embryonic primary ectodermal cells (Asashima et al., Roux's Arch Dev Biol. 198: 330–335 (1990); Smith et al., Nature 34S: 729–731 (1990)). Activin A can induce axial mesoderm in Xenopus and our group has shown that activin B is probably the endogenous inductor of axial structures in birds (Mitrani et al., Cell 63: 495–501 (1990)). Also very recently Mathews and Vale (1991) reported the cloning of the activin receptor. This receptor seems to have common features with other growth factor receptors but in contrast to others it is the first receptor to display serine kinase activity (Mathews et al., Cell 65: 973–982 (1991)).

Tumor Suppressor Genes are involved in the Control of Cell Proliferation

Tumor formation arises as a consequence of alterations in the control of cell proliferation and disorders in the interactions between cells and their surroundings that result in invasion and metastasis. A breakdown in the relationship between increase in cell number resulting from cell division and withdrawal from the cell cycle due to differentiation or cell death lead to disturbances in the control of cell proliferation. In normal tissues, homeostasis is maintained by ensuring that as each stem cell divides only one of the two daughters remains in the stem cell compartment, while the other is committed to a pathway of differentiation (Cairns, J., Nature 255: 197–200 (1975)). The control of cell multiplication will therefore be the consequence of signals affecting these processes. These signals may be either positive or negative, and the acquisition of tumorigenicity results form genetic changes that affect these control points.

It has now been possible to characterize some of these control points and to identify the genetic changes that contribute to malignancy. In the best-studied examples, changes at several different genes have been shown to occur within each tumor. These alterations affect genes concerned with positive stimuli to growth and genes whose products are normally involved in inhibition of cell growth (reviewed in Fearon, E. R. and Vogelstein, B., Nature 344: 868–870 (1990)).

Tumors have a defined Pattern of Growth

The patterns of growth of a variety of rapidly growing, transplantable and malignant tumors of epithelial origin are not random conglomerations of cells but organized tissues with characteristic histological patterns. The establishment of the basic pattern depends, first, on the connective-tissue-adjacent position of the mitotic cells, and second, on the distal movement, aging and finally death of the differentiated cells. In any tumor these normal rules persist. When growth begins a solid tumor typically consists of an outer sheath of connective-tissue-adjacent mitotic cells, a medial sheath of differentiated aging cells and an inner mass of dead cells. Except that the tumor forms a cyst instead of a sheet, the cells are stratified as they are, for instance, in the epidermis.

The picture presented by a typical solid tumor is consistent with a situation in which there is an excessive number of mitotic-cycle cells and an inadequate number of post-mitotic aging cells. Thus, cell production continues to exceed cell loss.

Removal of one Tumor accelerates Growth of a Second Identical Tumor

When two identical tumors are present, the removal of one accelerates the growth of the other (Goodman, G. J., *Proc. Amer. Assoc. Cancer Res.* 2: 207-(1957)); partial hepatectomy stimulates the growth of adenomatous hepatic nodules (Trotter, N. L., *Cancer Res.* 21: 778 (1961)). When two tumors of different tissue origins are present together in the same animal, they grow independently of each other so that each reaches its usual plateau as if the other was not present (Burns, E. R., *Growth* 33: 25 1969)). This last experiment neatly disproves the idea that tumor growth is inhibited by nutrient exhaustion or by toxic metabolic products. The most extensive studies of the plateau phenomenon in tumors are those of Bichel (Bichel, P., *Eur. J. Cancer* 6: 291 (1970); Bichel, P. *Eur. J Cancer* 8: 167 (1972); Bichel, P., *Nat. Cancer Inst. Mon.* 38: 197 (1973)), who carefully plotted the growth characteristics of three mouse ascites tumors, each derived from a different tissue and each reaching a stable plateau without killing its host. He found that the removal of tumor cells in the plateau phase causes the immediate resumption of growth of the remaining cell mass; that the cell-free ascites fluid, taken at the plateau phase and injected into another mouse, inhibits mitotic activity in tumor cells in the rapid growth phase, but only if these tumor cells are of the same type of tumor; that when two different tumors are grown simultaneously in the same mouse, each grows at its normal rate to reach its normal plateau irrespective of the presence of the other; and that, when two tumors are grown simultaneously in the same mouse, the cell-free ascites fluid from another mouse containing only one of the tumors inhibits the growth of only the same type of tumor leaving the other tumor to continue its uninhibited growth.

SUMMARY OF THE INVENTION

The subject invention relates to pharmaceutical preparations for manipulating proliferation of ectodermally-derived tissues, such as arising from hyperproliferative conditions or in connection with tissue repair. In general, the preparations comprise, as an active ingredient, an activin agonist in a pharmaceutically acceptable carrier or diluent. The invention also relates to methods of treating ailments marked by abnormal proliferation of ectodermally-derived tissue by use of the pharmaceutical preparations of the invention.

In preferred embodiments, the pharmaceutical preparations of the invention are intended for the treatment of proliferative skin disorders in which there is abnormal proliferation or growth of cells of the skin. For instance, the pharmaceutical preparations of the invention are intended for the treatment of hyperplastic epidermal conditions, such as keratosis or psoriasis, or proliferation of virally-infected cells. The subject method can also be employed to cause inhibition of hair growth, as for example, a way of reducing the growth of human hair as opposed to its conventional removal by cutting, shaving, or depilation, e.g. in the treatment of trichosis, as well as to protect hair follicle cells from radiation-induced death during cytotoxic therapies.

Other cutaneous disorders for which the subject activin therapies may be useful include the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin in particular, of dermatological diseases involving morbid proliferation and/or keratinization of the epidermis, as for example, caused by psoriasis or atopic dermatosis.

In yet other preferred embodiments, the subject method can be utilized to control proliferation of non-cutaneous epithelial cells, such as in conjunction with various periodontal procedures, corneal and other ocular procedures, and non-cutaneous plastic surgeries.

In preferred embodiments, the activin agonist preparations of the present invention are formulated for topical or subcutaneous application. Preferably, the preparations are in the form of an aqueous gel, water-dispersible lotion, or other pharmaceutically acceptable carriers, in the form of paste, tape or film support, or subcutaneous implants, preferably for the sustained release of the active ingredient. The preparations can also be in the form of sprays.

DETAILED DESCRIPTION OF THE INVENTION

The present invention relates to pharmaceutical preparations for controlling the proliferation of ectodermally-derived tissue, such as in the treatment of disorders marked by aberrant proliferation or in the repair of damaged tissue, which preparations comprise, as an active ingredient, an agent ("activin agonist") which mimics the inhibitory effect of activin or a related polypeptide factor, which activin agonist is provided in a pharmaceutically acceptable carrier or diluent. The invention also relates to methods of controlling proliferation of ectodermally-derived tissue by use of the pharmaceutical preparations of the invention.

For example, the subject method can be used in the treatment of disorders, or surgical or cosmetic repair of such epithelial tissues as skin and skin organs; corneal, lens and other ocular tissue; mucosal membranes; and periodontal epithelium. For instance, the methods and compositions disclosed herein provide for the treatment or prevention of a variety of damaged epithelial and mucosal tissues, particularly those resulting from hyperplastic or neoplastic conditions. It will be evident that the method will find ready application for the treatment or prophylaxis of psoriasis; keratosis; acne; comedogenic lesions; verrucous lesions such as verruca plana, plantar warts, verruca acuminata, and other verruciform lesions marked by proliferation of epithelial cells; folliculitis and pseudofolliculitis; keratoacanthoma; callosities; Darier's disease; ichthyosis; lichen planus; molluscous contagiosum; melasma; Fordyce disease; and keloids or hypertrophic scars. Activin formulations of the present invention may also be used as part of treatment regimens in autoimmune diseases for affecting healing of proliferative manifestations of the disorder, as for example, part of a treatment for aphthous ulcers, pemphigus such as pemphigus vulgaris, pemphigus foliaceus, pemphigus vegetans or pemphigus erythematous, epidermolysis, lupus lesions or desquamative lesions.

Furthermore, the subject method can be used to control wound healing processes, as for example may be desirable in connection with any surgery involving epithelial tissue, such as from dermatological or periodontal surgeries. Exemplary surgical repair for which activin therapy is a candidate treatment include severe burn and skin regeneration, skin grafts, pressure sores, diabetic ulcers, fissures, post surgery scar reduction, and ulcerative colitis.

In yet another aspect of the invention, preparations of activin agonist can be employed to control proliferation of oncogenically transformed cells. Many tumorigenic cells tend to undergo histological dedifferentiation following transformation, reverting to phenotypes which resemble embryonic or fetal cells, such as characterized by loss of contact inhibition and other growth restraints. As described in the appended examples, activin agonists can be used to inhibit proliferation of ectodermally-derived cells which have transformed phenotypes. For instance, as described in Example 8, activin A is capable of inhibiting proliferation of primary ectodermal cells. The inhibition of primary ectodermal cells by activin is significant in that these cells, though normal, are at a specific stage of development marked by a transformed phenotype, such as characterized by anchorage-independent growth. Accordingly, these cells have a malignant phenotype which may be equivalent to cancerous cells, e.g., as for example with respect to anaplastic and/or hyperplastic proliferation. To further illustrate, Example 10 demonstrates the inhibitory effect of an activin agonist on transformed epidermal cells.

The subject activin treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

For convienence, certain terms employed in the specification, examples, and appended claims are collected here.

The term "activin agonist" refers to molecules which inhibit proliferation of epithelial and other ectodermally-derived cells by mimicking the antiproliferative effects of activin A or a related activin factor. In particular, the term "activin agonist" encompasses polypeptides (such as preparations of activin-A itself) and peptidyl fragments thereof, as well as non-peptidyl mimetics and other organic molecules which bind to an activin or activin-related receptor of an ectodermally-derived cell and induce cell-cycle arrest of the treated cell. As used herein, the terms "activin-related polypeptide" and "activin-related factor" denote a family of polypeptides related to activin-A by both sequence homology and structure, and include such polypeptide factors as activin-B.

The term "ectoderm" refers to the outermost of the three primitive germ layers of the embryo; from it are derived the epidermis and epidermal tissues such as the nails, hair and glands of the skin, the nervous system, external sense organs and mucous membrane of the mouth and anus.

The terms "epithelia" and "epithelium" refer to the cellular covering of internal and external body surfaces (cutaneous, mucous and serous), including the glands and other structures derived therefrom, e.g., corneal, esophagal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, which that characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

The term "stomodeal tissue" refers to epithelial tissue derived from rostral ectoderm of an embryo, e.g. which becomes the front part of the mouth. Exemplary stomodeal tissue includes oral or paraoral epithelial tissue, and periodontal epithelial tissue.

The term "proctodeal tissue" refers to epithelial tissue of ectodermal origin and derived from structures at the caudal end of the embryo, e.g., anorectal tissue.

The term "auditory tissue" refers to ectodermally-derived tissue which is formed from the auditory vesicle, e.g. tissue of the inner ear.

The term "nasal tissue" refers to nasal and olfactory epithelium.

Furthermore, the term "epithelioid cells" refers to cells which have phenotypes resembling epithelial cells. For instance, epithelioid cells can be cells from an epithelioma or other epitheliomatous cells, e.g. any tumor derived from epithelium, such as a carcinoma.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Another carcinomatous epithelial growth is "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

The term "nail" refers to the horny cutaneous plate on the dorsal surface of the distal end of a finger or toe.

The term "gland" refers to an aggregation of cells specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface. The ordinary or eccrine sweat glands are distributed over most of the body surface, and promote cooling by evaporation of the secretion; the apocrine sweat glands empty into the upper portion of a hair follicle instead of directly onto the skin, and are found only in certain body areas, as around the anus and in the axilla.

The term "hair" (or "pilus") refers to a threadlike structure, especially the specialized epidermal structure composed of keratin and developing from a papilla sunk in the corium, produced only by mammals and characteristic of that group of animals. Also, the aggregate of such hairs. A "hair follicle" refers to one of the tubular-invaginations of the epidermis enclosing the hairs, and from which the hairs grow; and "hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis, such as "epidermodysplasia verruciformis", which is a condition due to a virus identical with or closely related to the virus of common warts. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

As used herein, "proliferating" and "proliferation" refer to cells undergoing mitosis.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

A "patient" or "subject" to be treated by the subject method can mean either a human or non-human animal.

The term "cosmetic preparation" refers to a form of a pharmaceutical preparation which is formulated for topical administration.

An "effective amount" of an activin agonist, with respect to the subject method of treatment, refers to an amount of agonist in a preparation which, when applied as part of a desired dosage regimen, provides inhibition of cell proliferation so as to reduce or cure a proliferative disorder according to clinically acceptable standards.

In one aspect of the present invention, the pharmaceutical preparations are intended for the treatment of cutaneous diseases in which there is abnormal proliferation or growth of cells of the skin. For instance, the pharmaceutical preparations of the invention are intended for the treatment of hyperplastic epidermal conditions, such as keratosis, or for inhibition of hair growth, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Normal skin epidermis is a complex epithelial tissue containing keratinocytes that are proliferating, differentiating and desquamating, and is stratified such that morphological and functional changes in the keratinocytes occur in an orderly progression. More specifically, the basal layer of the epidermis contains proliferating keratinocytes which synthesize DNA, while the superbasal layers of the epidermis contain highly differentiated keratinocytes which degrade DNA. Thus, the normal epidermis is maintained in a dynamic steady state as proliferation of keratinocytes continually compensates for the loss of cells which are shed from the surface of the skin.

Many common diseases of the skin, such as psoriasis, squamous cell carcinoma, keratoacanthoma, actinic keratosis and warts, are characterized by localized abnormal proliferation and growth. For example, in psoriasis, which is characterized by scaly, red, elevated plaques on the skin, the keratinocytes are known to proliferate much more rapidly than normal and to differentiate less completely.

The theoretical necessity for growth inhibitors as factors necessary for the control of epithelial homeostasis has long been postulated (Bullough et al., Proc. Roy. Soc. B. 151: 517–536 (1960); Weiss et al., J. Physiol. 41: 1–47 (1957)). There is strong evidence for negative growth factors as key regulators in this process. Yet the nature of the molecules involved has not been fully identified. As will be shown in the Examples hereafter, activin mRNA is shown to be present in human keratinocytes grown in culture. In situ hybridization experiments indicate that in normal human skin, activin A mRNA expression is distributed throughout the epidermis but becomes stronger towards the basal layer. It will also be shown that following treatment with activin A, skin organ cultures show a decrease of thymidine incorporation in the epidermis. These results indicate that activin A may be directly involved in the control of growth and differentiation of epidermal tissues.

The results of the experiments presented in the Examples clearly indicate that treatment of various hyperproliferative epidermal conditions can diminish the proliferation rate of epidermal cells. Moreover, the appended examples also demonstrate that activin A can inhibit proliferation of transformed epidermal cells. The preparations of the present invention can thus also be employed in the treatment of neoplastic/hyperplastic epidermal conditions.

However, it should be borne in mind that although other growth factors, even closely related ones, may also be expressed in the epidermis and other epithelial tissue, each factor probably acts in a very specific manner, such as in a tissue- or cell-type specific manner. For instance, preliminary data suggest that a paracrine factor closely related to activin-A, namely activin-B, is expressed in other types of epithelia where activin-A is absent. Accordingly, depending on the response of the particular tissue to an activin-like paracrine factor, the preparation of activin agonist can be formulated to include, for example, activin-A or activin-B, or mimetics thereof.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of an activin agonist can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with activin can be used to reverse the pathological epidermal activiation and can provide a basis for sustained remission of the disease.

A variety of other keratotic lesions are also candidates for treatment with the subject activin agonist preparations. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of activin agonist compositions in amounts sufficient to inhibit hyperproliferation of epidermal/epidermoid cells of the lesion.

Another cutaneous disorder of interest, rosacea, is an inflammatory disease due to abnormal sensitivity of the vasculature. Rosacea often results in secondary sebaceous gland hyperplasia and inflammation producing characteristic skin lesions. Prior art treatments for rosacea have generally involved the use of antiinflammatory antibiotics such as metronidizole. The present invention contemplates a therapeutic regimen for rosacea which includes activin treatment to inhibit hyperplasia, particularly of glandular epithelial cells.

Acne represents yet another dermatologic ailment which may be treated with an activin agonist. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by Propinobacterium acnes and Staphylococcus epidermidis bacteria and Pitrosporum ovale, a yeast. Treatment with activin, particularly topical preparations, may be useful for preventing the transitional features of the ducts, e.g. hypercornification, which lead to lesion formation. The activin agonist treatment may further include, for example, antibiotics, retinoids and antiandrogens.

Activin agonist preparations of the present invention can also be used for the treatment of cutaneous proliferations that are benign or malignant, which are either of viral origin such as common warts, plane warts or epidermodysplasic verruciform, or which are a result of other cellular transforming and/or immortalizing events, such as may be induced by radiation.

An exemplary ailment which may be treated with an activin agonist is Bowen's disease, a disorder characterized as a superficial intraepidermal tumor of keratinocytes most commonly caused by ultraviolet irradiation. Approximately 5% of Bowen's disease tumors metastasize as squamous cell carcinoma. These tumors frequently cover large areas of the skin. Current treatments consist of excisional and cryosurgery and 5-fluorouracil cream. As above, the subject activin treatment can augment or supersede present therapies for inhibiting proliferation of transformed keratinocytes.

Warts are known to be intra-epidermal tumors of the skin caused by infection with viruses such as papillomaviruses. Papillomaviruses (PV) have been linked to widespread, serious human diseases, especially carcinomas of the genital and oral mucosa. Papillomaviruses can induce benign, dysplastic and malignant hyperproliferations of skin and mucosal epithelium (see, for example, Mansur and Androphy, (1993) Biochim Biophys Acta 1155:323–345; Pfister (1984) Rev. Physiol. Biochem. Pharmacol. 99:111–181; and Broker et al. (1986) Cancer Cells 4:17–36, for reviews of the molecular, cellular, and clinical aspects of the papillomaviruses). The human papillomaviruses (HPV) are a heterogeneous group of DNA tumor viruses associated with hyperplastic (warts, condylomata), pre-malignant and malignant lesions (carcinomas) of squamous epithelium. Tens of millions of women suffer from HPV infection of the genital tract. Significant number of these women eventually develop cancer of the cervix. It has been estimated that perhaps twenty percent (20%) of all cancer deaths in women worldwide are from cancers which are associated with HPV, and as many as 90% of all cervical cancer maybe linked to HPV. In light of the present invention, proliferation of PV-infected cells, especially PV-transformed cells, can be inhibited by a treatment protocol which includes administration of activin agonist compositions.

Activin agonists can also be used in the treatment of other epithelial proliferative disorders caused by wart viruses. For example, bowenoid papulosus is a tumor of the genitalia induced by premalignant wart viruses and usually afflicting men. Condylomatous dysplasia and cervical carcinoma in situ are premalignant tumors of the female genitalia, also induced by wart viruses. Known treatments for all three of these tumors include cryosurgery, 5-fluorouracil, trichloroacetic acid, podophyllin and interferon. These treatments are painful, however, and not always effective. According to the present invention, such therapies can be augmented or replaced by treatment with the subject activin agonist preparations.

The present invention also provides a method for treating various forms of dermatitis. Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, activin agonist preparations can be used in the treatment and/or prevention of certain symptoms of dermatitis caused by unwanted proliferation of epithelial cells. Such activin therapies for these various forms of dermatitis can also include topical and systemic corticosteroids, antipuritics, and antibiotics.

Also included in ailments which may be treated with activin agonist are disorders specific to non-humans, such as mange.

Yet another aspect of the present invention relates to the use of activin agonist preparations to control hair growth. The growth of hard keratin fibers such as wool and hair is dependent on the proliferation of dermal sheath cells. Hair follicle stem cells of the sheath are highly active, and give rise to hair fibers through rapid proliferation and complex differentiation. The hair cycle involves three distinct phases: anagen (growing), catagen (regressing), and telogen (resting). The epidermal stem cells of the hair follicle are activated by dermal papilla during late telogen. This is termed "bulge activation". Moreover, such stem cells are thought to be pluripotent stem cells, giving rise not only to hair and hair follicle structures, but also the sebaceous gland and epidermis. As described in the appended examples, the subject method provides a means for altering the dynamics of the hair growth cycle to induce quiescence of proliferation of hair follicle cells, particularly stem cells of the hair follicle.

For instance, activin treatments can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, activin can be used to manage hirsutism, a disorder marked by abnormal hairiness. Activin therapy can also provide a process for extending the duration of depilation.

Moreover, because activin is generally cytostatic to epithelial cells, rather than cytotoxic, it can be used to protect hair follicle cells from cytotoxic agents which require progression into S-phase of the cell-cycle for efficacy, e.g. radiation-induced death. Treatment with an activin agonist provides protection by causing the hair follicle cells to become quiescent, e.g., by inhibiting the cells from entering S phase, and thereby preventing the follicle cells from undergoing mitotic catastrophe or programmed cell death. For instance, activin treatments can be used for patients undergoing chemo- or radiation-therapies which ordinarily result in hair loss. By inhibiting cell-cycle progression during such therapies, activin treatment can protect hair follicle cells from death which might otherwise result from activation of cell death programs. After the therapy has concluded, activin treatment can also be removed with concommitant relief of the inhibition of follicle cell proliferation.

The subject method can also be used in the treatment of folliculitis, such as folliculitis decalvans, folliculitis ulerythematosa reticulata or keloid folliculitis. For example, a cosmetic prepration of an activin agonist can be applied topically in the treatment of pseudofolliculitis, a chronic disorder occurring most often in the submandibular region of the neck and associated with shaving, the characteristic lesions of which are erythematous papules and pustules containing buried hairs.

In similar fashion, activin agonist preparations can be used in the treatment of granulomas, e.g. tumor-like mass or nodule of granulation tissue, which may include epithelial tissue derived from cutaneous or mucosal sources.

In another aspect of the invention, the subject method can be used in conjunction with various periodontal procedures in which inhibition of epithelial cell proliferation in and around periodontal tissue is desired. For example, activin preparations of the present invention can find application in the treatment of peridontal disease. It is estimated that in the United States alone, there are in excess of 125 million adults with periodontal disease in varying forms. Periodontal disease starts as inflammatory lesions because of specific bacteria localizing in the area where the gingiva attaches to the tooth. Usually first to occur is a vascular change in the underlying connective tissue. Inflammation in the connective tissue stimulates the following changes in the epithelial lining of the sulcus and in the epithelial attachment: increased mitotic activity in the basal epithelial layer; increased producing of keratin with desquamation; cellular desquamation adjacent to the tooth surface tends to deepen the pocket; epithelial cells of the basal layer at the bottom of the sulcus and in the area of attachment proliferate into the connective tissue and break up of the gingival fibers begins to occur, wherein dissolution of the connective tissue results in the formation of an open lesion. The application of activin preparations to the periodontium can be used to inhibit proliferation of epithelial tissue and thus prevent further periodontoclastic development.

The present treatment can also be effective as part of a therapeutic regimen for treating oral and paraoral ulcers, e.g. resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, lend the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of an activin agonist can reduce the abnormal proliferation and differentiation of the affected epithelium, helping to reduce the severity of subsequent inflammatory events.

Furthermore, it will be understood that the subject activin agonist preparations can be used to treat anomalies resulting from proliferation of tracheobronchial and nasal epithelial cells. For instance, activin can be used to prevent growth of tracheaobronchial tumors. Likewise, trachael stenosis resulting from squamous metaplasia of the mucosal columnar epithelial can be controlled with activin therapy.

Yet another aspect of the present method concerns the use of activin agonist preparations for controlling tissue repair after surgery and remodelling following injury. In one embodiment, the subject activin agonist preparations can be used to help control guided tissue regeneration, such as when used in conjunction with bioresorptable materials. For example, incorporation of periodontal implants, such as prosthetic teeth, can be facilitated by activin treatment. Reattachment of a tooth involves both formation of connective tissue fibers and re-epithelization of the tooth pocket. Activin treatment can be used to accelerate connective tissue reattachment by inhibiting the mitotic function of basal epithelial cells in early stages of wound healing.

Furthermore, activin agonists can be used to attenuate cosmetic damage by providing more particular control over proliferation of epidermal cells such that keloidal scarring can be avoided during connective tissue repair, including dermatoplasty. In similar fashion, activin agonist preparations can be used to control the rate of proliferation of epithelial cells during other plastic surgery procedures, including proctoplasty and rhinoplasty.

In yet another embodiment, the subject activin agonist preparations can be used to control lens epithelial cell proliferation to prevent post-operative complications of extracapsular cataract extraction.

Cataract, frequently in aged people, is an intractable eye disease and various studies on a treatment of cataract have been made. But at present, the treatment of cataract is finally attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing an activin agonist preparation into the anterior chamber of the eye after lens removal. Furthermore, the solution containing activin agonist can be osmotically balanced to provide minimal effective dosage when instilled into the anterior chamber of the eye, thereby inhibiting subcapsular epithelial growth with some specificity.

Activin agonist preparations can also be used in the treatment of corneopathies marked by corneal epithelial cell proliferation, as for example in ocular epithelial disorders such as epithelial downgrowth or squamous cell carcinomas of the ocular surface.

The source of activin agonist to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of activin and activin-related polypeptides. Recombinant sources of activin agonists are also available. For example, the gene encoding activin A and other activin-related paracrine factors, are known, inter alia, from European Patent Application No. 222,491, and from U.S. Pat. Nos. 5,286,654, 5,071,834 and 4,798,885.

Those of skill in treating disorders which are characterized by an excessive proliferation and/or abnormal differentiation of epithelial tissues can determine the effective amount of an activin agonist to be formulated in a pharmaceutical or cosmetic preparation. In general it is contemplated than an effective amount would be from 0.001 mg/kg to 50 mg/kg body weight and more preferably from 0.01 mg/kg to 10 mg/kg body weight. In one embodiment, the biologically active ingredient contained in the preparations is in the range of 3 to 300 ng per gram preparation, though higher or lower amounts might also be effectively employed.

The activin agonist formulations using the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular activin agonist as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeuitcs, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the activin agonist compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the inhibition of hair growth, and as such, are to be considered cosmetic compositions. Cosmetic compositions known in the art, preferably hypoallergic and pH controlled are especially preferred, and include toilet waters, packs, lotions, skin milks or milky lotions. Said preparations contain, besides the activin agonist, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the activin agonist, will be incorporated in said compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage. The humectant, surfactant, oil, etc. . . . referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the activin agonist is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of an activin protein and other peptidyl agonist are encapsulated in the aqueous spaces between the molecular layers. The lipid soluble active ingredient of activin agonist, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of activin agonist is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated activin agonist can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanolamine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

The liposome-formulated forms of the activin agonist, particularly those obtained in the above-referred method of preparing such liposome formulated forms, may be used as such or in combination with any of the aforementioned carriers to prepare ointments, creams, gelees, toilet waters, etc.

Apart from the above-described compositions, use may be made of covers, e.g. plasters, bandages, dressings, gauze pads and the like, containing an appropriate amount of a composition as referred hereinabove. In some cases use may be made of plasters, bandages, dressings, gauze pads and the like which have been impregnated or sprinkled with a topical formulation containing the activin agonist, e.g. with an aseptic aqueous solution, or strewn with a powdery solid composition, or smeared, covered or coated with a semi-liquid composition.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1

Activin-βA but not Activin-βB can be amplified by PCR from Guinea-Pig and Human Epidermis PCR was performed initially on cDNA obtained by reverse transcribing mRNA from guinea-pig keratinocytes using primers A1 and P1. A small volume of the PCR reaction was reamplified using instead primers V1 and A2. The fragment obtained (GKA) was sequenced directly (Mitrani et al., Cell 63: 495–501 (1990)) and found to be 100% identical at the amino acid level to human activin βA chain in the region sequenced and 90% identical at the DNA level. The same procedure was repeated using instead total RNA derived from normal human keratinocytes grown in culture for a period of three weeks. A 270 bp fragment (HKA) was obtained which, upon direct sequencing, showed 100% similarity to human activin βA chain at the DNA level. Even though the primers used to isolate the activin genes could also bind to the activin βB chain (Thomsen et al., Cell 63: 485–493 (1990); Mitrani et al., Cell 63: 495–501 (1990)), direct sequencing revealed only the single βA component. The detailed method is as follows:

RNA Preparation

Total RNA was prepared as described previously (Mitrani et al., Cell 63: 495–501 (1990)). RNA was prepared from normal primary human and guinea pig keratinocytes grown in culture for different periods. In addition, RNA was prepared from the cell line SCL-1 of epidermal origin. Briefly, the cells were digested in proteinase K (200 µg/ml) at 45° C. for 45 minutes. The digest was extracted twice with phenol chloroform and precipitated in 0.3M sodium acetate and 2 volumes of ethanol.

Total nucleic acids were resuspended in 10 mM Tris.HCl/ 10 mM $MgCl_2$, and digested with DNAse I (10 µg/ml) for 30 minutes at 37° C. in the presence of RNAsin (Promega).

Reverse Transcription

About 1–2 µg of total RNA were precipitated, resuspended in 4 µl of $H_2O$, 4 µl of reverse transcription buffer (BRL), 1 µl of cloned MMLV reverse transcriptase (BRL 200 units/µl), 1 µl of oligo dT primer (1 µg/µl), and 2.5 mM dNTPs in 10 µl $h_2O$ were added and the reaction was incubated at 37° C. for one hour. After this the reaction mixture was divided into 1–2 µl aliquots and stored at −70° C. until used directly in a PCR reaction.

Activin Primers for PCR Reactions

Degenerate primers that encompass sequences coding for both activin chains βA and βB were created with a linker added at each end. The 5'-end primer (A1) has a BamHI site. The 3'-end primer (A2) has an EcoR1 site. A1 was designed to target a region which is highly specific to the activin genes, as all other members of the TGF-β superfamily include extra amino acids in this region. V1 and V2 represent primers for detecting/amplifying members of the Vg subfamily.

The primers used for the PCR reactions are as follows:

A1: 5'-GG(AGCT)(TC)(AGCT)GA(AG)TG(TC)GA(TC)GG-3'
A2: 5'-(AG)CA(AGCT)CC(AG)CA(TC)TC(TC)TC(AGCT)AC(AGT)AT-3'
V1: 5'-TGG(CAG)A(AGCT)GA(TC)TGGAT(ATC)(GA)T(AGCT)GC-3'
V2: 5'-TTCTAGA(A/G)NGT(C/T)TGNAC(T/A/G)ATNGC(A/G)TG-3'
P1: 5'-AGATCTGATATCATCGATGAATTCTTTTTTTTTTTTTTTTTT-3'
(SEQ ID No. 5)

PCR on whole cDNA populations.

PCR was performed as described previously (Mitrani et al., Cell 63: 495–501 (1990)). For the first round 40 cycles each containing a denaturation step at 94° C. for 30 sec, annealing at 37° C. for 40 sec and elongation at 72° C. for 1 minute were performed. The second round of amplification was done for 35 cycles under the same conditions. The fragment was separated by electrophoresis and sequenced directly as described previously (Mitrani et al., Cell 63: 495–501 (1990)). For each PCR reaction 0.2 µl of 10× Taq buffer (Promega), 1 µl of 10 mM dNTPs, 2 ul of primer mix containing about 1 µg of each primer and 12 µl of deionized water were mixed on ice. 2 µl of DNA template were then added to each tube. The reactions were performed in three steps: denaturation at 94° C. for 30 sec, annealing at 37° to 44° C. for 1 minute, and elongation at 72° C. for 1 minute. This cycle was repeated forty times using a PCR cycler (Ericomp USA).

Preparation of Single Stranded labeled DNA

A small amount (1–5 ng) of gel purified template DNA was mixed with 2 µl of 10× Taq buffer (Promega), 40 µCi (3000 Ci/mmol) 32p dATP, 200 µM of dGTP, dCTP, dTTP, 2 units of Taq polymerase (Promega) and the required 3'-end primer at 10 nM in a 20 µl reaction. The reaction was performed for 30 cycles of linear amplification, denaturation (94° C. for 30 sec), annealing (50° C. for 1 min) and elongation (72° C. for 1 min). $6 \times 10^7$ DPM per ng of template are obtained by this method. Two separate probes were prepared from the chick activin βB. The first was prepared using primers VI and A2 to prepare the template cAB. The second βB probe was prepared from a smaller fragment obtained by PCR amplification of cAB using primers V1 and B2.

Direct Sequencing

DNA was sequenced directly after gel purification using the technique described by Winship (Winship, P. R., Nucleic Acids Research 17: 1266 (1989)). $^{32}$P-dATP was used as marker. Gels were covered with saranwrap, and exposed directly to film for 12–24 hours

EXAMPLE 2

Activin βA RNA is expressed in Normal but not in Transformed Keratinocytes

The human activin βA fragment HKA was used as template to prepare single stranded DNA and RNA antisense probes to be used in Northern blot analysis (Mitrani et al., Cell 63: 495–501 (1990)). On RNA derived from cultures of normal differentiated human keratinocytes two transcripts of 3.4 and 2.8 kb in size (Albano et al., Development 110: 435–443 (1990); Murata et al., Proc. Natl. Acad. Sci. USA 85: 2434–2438 (1988)), were readily seen. RNA was also prepared from a transformed line of epidermal origin SCL-1 (Boukamp et al., Cancer Res. 45: 5582–5592 (1985)), which, when hybridized to the activin-βA probe, gave no detectable signal. When the same blot was rehybridized with a probe coding for TGF-β2, a signal of about the same intensity was detected on both lanes, however, no signal was detected, under the same stringency conditions, when an activin βB probe was used instead.

The detailed method is as follows:

Northern Blot Analysis

Northern blots were prepared as described previously (Mitrani et al., Cell 63: 495–501 (1990)). Briefly, RNA was prepared as described above, denatured, electrophoresed on a 1% agarose/formaldehyde gel, transferred to a GeneScreen nylon membrane (Dupont) crosslinked with W and hybridized to the different activin probes. Northern blots were reexamined using the RNA riboprobes. This allowed performing the hybridization conditions at higher stringency For this case the blots were hybridized at 55° C. in 50% formamide. Washes were at 68° C. in 0.1×SSC and 0.1% SDS.

EXAMPLE 3

Activin βA RNA is expressed in Normal Human Epidermis

In order to localize the expression of activin BA in human skin, in situ hybridization experiments were performed (see, Rogers, M. and Zeller, R., *Current Protocols in Molecular Biology*, F. Ausbel et al., Eds., John Wiley & Sons. Interscience, New York). When human skin sections were hybridized with the HKA antisense probe, significant hybridization was observed in most cells of the epidermis up to the stratum granulosum, with the signal becoming stronger in the lower layers including the stratum basal. No signal was detected with the sense probe.

Hybridization Conditions

Hybridization solution contained: 50% formamide, 5×SSC, 1×Denhardts solution, 0.1 mg/ml Salmon sperm DNA and 1×10$^6$ dpm/ml of the p$^{32}$ labelled probe. Hybridization was at 42° C. Washes were 3 times, 20 minutes each with 50% formamide at 42° C.

EXAMPLE 4

Activin inhibits Proliferation of Keratinocytes in Culture

Activin containing medium (ACM) was prepared from conditioned medium from p388D1 cells as described previously (Thomsen et al., *Cell* 63: 485–493 (1990)). Activin A was resuspended in water at 30 ng/ml and added directly to the culture medium. Activin was found to be effective at concentrations of 15 to 30 pM.

Results indicate that ACM inhibits proliferation of both guinea-pig and human keratinocytes grown in culture on mitomycin-c-treated 3T3 feeder layers (Rheinwald, J. A., *Meth. in Cell. Biol.* 21A: 229–254 (1980); Green, H., Harvey Lectures series, 74, 101, 139 (1979)) (Table 1). ACM did not inhibit proliferation of normal 3T3 cells grown separately. Keratinocytes obtained by trypsinization were plated and grown in monolayer cultures; Rheinwald, J. A., *Meth. in Cell. Biol.* 21A: 229–254 (1990); Green, H., Harvéy Lectures series, 74, 101, 139 (1979)).

TABLE 1

| Effect of ACM on thymidine incorporation into keratinocytes grown in monolayer cultures | | | | |
|---|---|---|---|---|
| | Control DPM/10$^3$ cells | % | ACM DPM/10$^3$ cells | % |
| Human epidermis | 1330 | 100 | 585 | 44 |

EXAMPLE 5

Activin inhibits Proliferation of Guinea-Pig Keratinocytes in Skin Organ Culture Guinea-pig skin explants were grown in monolayer cultures in the presence or absence of activin containing medium (ACM). DNA synthesis, as measured by thymidine incorporation was significantly lower in the epidermis of ACM-treated skin explants than in control explants. In contrast, thymidine incorporation- was significantly higher in the dermis of ACM-treated skin explants than in untreated controls (Table 2).

TABLE 2

| Effect of ACM on thymidine incorporation into guinea-pig epidermis cells from skin organ cultures | | | | |
|---|---|---|---|---|
| | Control DPM/mg | % | ACM DPM/mg | % |
| Guinea-Pig epidermis n | 4668 5 | 100 | 3604 8 | 77 |

EXAMPLE 6

Activin inhibits Proliferation of Human Keratinocytes in Skin Organ Cultures Human skin explants were grown in monolayer cultures in the presence or absence of activin containing medium (ACM). DNA synthesis, as measured by thymidine incorporation was significantly lower in the epidermis of ACM-treated skin explants than in control explants. In contrast, thymidine incorporation was significantly higher in the dermis of ACM-treated skin explants than in untreated controls (Table 3).

TABLE 3

| Effect of ACM on thymidine incorporation into human epidermal cells from skin organ cultures | | | | |
|---|---|---|---|---|
| | Control DPM/mg | % | ACM DPM/MG | % |
| Human epidermis n | 1419 6 | 100 | 926 7 | 65 |

Detailed Methods for Examples 5 and 6

In Vitro Skin Organ Cultures

Both guinea-pig and human skin organ explants were grown in culture in the presence or absence of ACM. Results show thymidine incorporation as DPM/mg tissue, expressed also as percentage of untreated controls. n=No. of experiments. Ears from young (100–200 gr) guinea pigs were shaved with a scalpel and immersed 60 sec in 70% ethanol. Lower and upper skins were separated from the cartilage. Fat as well as excess dermal tissue were removed and the skin was cut into 0.5–1 cm$^2$ pieces. Similarly, human foreskins (24 hours post operation from individuals one to twenty years old) were rinsed in 70% ethanol, scraped with a scalpel on the external side and trimmed from supporting subdermal and some dermal tissue. All skin explants were grown under the same culture conditions. For each experiment skin explants were all derived from the same source and cultured, two explants per 35 mm petri dishes in 2 ml of DMEM containing 10% FCS, and 0.5 µg/ml hydrocortisone. ACM-treated dishes received in addition either 20% XTC-CM (Smith et al., *Nature* 345: 729–731 (1990)) or 0.5% PIF (Albano et al., *Development* 110: 435–4a,3 (1990)). Dishes were cultured for 24 to 96 hours at 37° C. and 5% CO$_2$ with gentle shaking. The culture medium was changed every 36 hours. 12–14 hours before termination of the experiment $^3$H-thymidine (Amersham, 5 µCi/ml, 80 Ci/mMole) was added to the cultures. Explants were then removed, washed with cold PBS and incubated in 2M CaCl$_2$ containing 10 mM non-labeled thymidine for 2 hours. The epidermis becomes loosened by this treatment and was removed as a sheet into Whatman paper for drying excess fluid. The dermal pieces were also dried this way and both tissue types were weighed and processed further. The tissues were then washed three times with agitation in 0.5%; Triton X-100 solution containing 2 mM $MgCl_2$ and 10 mM thymidine to remove most (>95%) of the non-bound thymidine. Tissues were then incubated for 6 hours at 37° C. in 10 mM Tris pH 7.4, containing 1 mM $MgCl_2$, 0.1% Triton X-100 and 2 μg/ml DNAse (type I crystallized, Boehringer-Mannheim). Both the digesting solution and the digested tissues were counted in scintillation fluid. More than 90% of the $^3$H-thymidine was found to be removed from the tissues into the DNAse solution by this procedure. DNAse-solubilized counts were expressed per mg of tissue and shown as percentage of untreated controls.

EXAMPLE 7

Recombinant Activin A inhibits Proliferation of Skin Explants

In experiments similar to those described above in Examples 5 and 6, guinea pig skin, mouse skin and human skin explants were treated with preparations of recombinant human activin A. Briefly, skin explants were grown in DMEM supplemented with brdU, penicillin (100 U/ml), streptomycin (100 ug/ml) and recombinant human acitivin A (Genentech, San Fransico) at varying concentrations, at 37° C. in 5% $CO_2$, shaking for periods of 2 to 8 days. Medium, pluc activin if present, was changed every two days. Such explant cultures seem to reflect the behavior of skin under extreme, but controlled, wound healing conditions. For instance, the rate of keratinocyte proliferation is about ten fold higher than the normal rate. However, addition of recombinant activin A reduces the number of brdU-incorporating cells. For example, recombinant human activin A, at a concentration of 50 ng/ml, inhibited brdU incorporation by up to 75% in keratinocytes of the explants, when compared to untreated controls.

EXAMPLE 8

Activin inhibits Proliferation of Primary Ectodermal Cells

Activin inhibits c-myc Expression in Early Embryonic Chick Cells in Culture

Stage X-XIII blastoderms were dissected, dissociated by trypsin treatment and plated on culture plates containing RPMI medium and 10% FCS at a concentration of 100,000 cells/ml. Some of the cultures were supplemented with activin at different concentrations, when plated. After 24 hrs in culture, the cells were fixed and immunostained with a polyclonal anti-human c-myc antibody, followed by flourescein-conjugated goat anti rabbit serum. In cultures grown in the absence of activin, nuclear staining is seen mostly in multilayer areas. Cultures supplemented with 6 ng/ml activin immunostained like the control cultures, while in cultures supplemented with 60 ng/ml activin, no staining was detected, suggesting inhibition of c-myc expression. When pooled pre-immune rabbit serum was used instead of the anti c-myc antibody, as a control, no signal was detected. DNA Synthesis in Primary Cell Cultures in the Presence or Absence of Activin In order to examine the effect of activin on the DNA synthesis in primary cultures of early chick embryonic cells, cells derived from stage X-XIII blastoderms (see above) were grown in monolayer cultures for 21 hrs after which 0.1 mM of BrdU was added to the culture medium. After another 3 hrs, cells were fixed, treated with 2M HCl and immunostained with monoclonal antibody against BrDU. Activin was added to some of the cultures at different concentrations (36, 60 or 360 ng/ml).

In cells that were grown without activin and plated at 100,000 cells/ml, nuclear staining was most evident in regions where the concentration of cells was the highest and a second sheet of cells was starting to form, mostly in the central cells of the patch. Similar to the c-myc expression pattern described above, no staining was observed in sparsely grown cells. In cells that were plated at higher concentration, 300,000 cells/ml, nuclear staining was seen also in cells grown in less dense areas. Treatment of the cells with activin (36, 60 or 360 ng/ml) caused complete inhibition of proliferation when the cells were plated at 100,000 cells/ml, while in cultures grown at the higher concentration, activin treatment (60 ng/ml) caused only partial inhibition and some stained nuclei were seen.

Anchorage Independent Growth

The ability of cells to grow in a semi-solid medium is often associated with an undifferentiated state and mostly with tumorigenicity. Thus, factors that influence this process may have a role in determining the differentiation state of the cells. The early embryonic cells from pre-gastrulation stages can grow in semi-solid medium, but quickly loose this property after gastrulation. In the following experiments, the ability of activin and other factors to stimulate or inhibit this property were examined.

Semi-solid agar, to which the tested factor was added, was mixed before gelling with dissociated cells from stage X-XIII blastoderms. The cells were grown for 3 days after which clones of 5–20 cells with cytoplasmatic extensions were recorded. The supplement of FCS to the agar was found to be very important for this type of growth. If 10% FCS was added to the agar, a cloning efficiency of about 20% was obtained while only few rather small clones were obtained in the absence of FCS. Several peptide growth factors were examined either with or without FCS. EGF (0.5–500 ng/ml), FGF (25 ng/ml), TGF-β1 (0.6–60 ng/ml), TGF-β2 (20 ng/ml) were not found to affect cloning efficiency. In contrast recombinant human activin A (60 ng/ml) inhibited the number of clones dramatically.

About 10 fold decrease were seen in the number of typical clones after activin treatment. Lower doses of activin (6 ng/ml) were ineffective in inhibiting colony formation (Table 4).

TABLE 4

The effect of Activin A on AIG of early chick embryonic cells

| Origin of Cells | 10% of FCS | Activin A | Cloning efficiency |
|---|---|---|---|
| XI-XIII | – | — | — |
| XI-XIII | – | 60 ng/ml | — |
| XI-XIII | + | — | >10% |
| XI-XIII | + | 6 ng/ml | >10% |
| XI-XIII | + | 60 ng/ml | — |

EXAMPLE 9

It has also been found that Activin A RNA is not expressed in SCL-1 cells, a transformed line of epidermal origin.

EXAMPLE 10

Activin A can inhibit Proliferation of SCL-1 Cells grown in Culture

SCL-1 cells were grown in monolayer cultures in the presence or absence of ACM. DNA synthesis as measured by thymidine incorporation was significantly lower in ACM-treated cells than in control cells (Table 5). Cells were grown as described previously (Boukamp et al., *Cancer Res.* 45: 5582-5592 (1985)).

TABLE 5

Effect of ACM on thymidine incorporation into transformed human epidermal cells scl-1

|  | Control DPM/mg | % | ACM DPM/mg | % |
|---|---|---|---|---|
| Human SCL-1 cells | 972 | 100 | 715 | 71 |
| n | 6 |  | 6 |  |

EXAMPLE 11

Activin βA RNA is expressed in Human Hair Follicle Cells

Facial hair follicles from adult volunteers were removed by plucking after washing the face with detergent and 70% ethanol. Individual hairs containing the follicle were carefully introduced into a 10 ul drop of RNAzol (Biotecx Laboratories, Inc.), taking care that only the deeper part of the follicle came in contact with the solution. Between ten to twenty individual hairs were extracted in this manner. The mixture was treated with 2 ul of chloroform and kept on ice for 30 min, centrifuged at 15 kg for 15 min at 4° C., and the aqueous phase collected and used to prepare cDNA.

RNA from as little as ten to twenty isolated hair follicles was prepared, reverse transcribed and amplified by PCR Using primers A1 and A2 and primers Vg1 and Vg2 as described above. Two corresponding fragments were obtained which, after sequencing, were identified as coding for activin βA and for BMP-6. The observations suggest that the same paracrine factors that are expressed in epidermis, are also transcribed by the follicle cells. Significant difference in behavior between these two regions may be attributed to each being under different mesenchymal influences, e.g. proteins produced by the dermis may also be important during hair follicle morphogenesis and growth.

EXAMPLE 12

Effect of Activin on Proliferation of Hair Follicles

Figure 1:
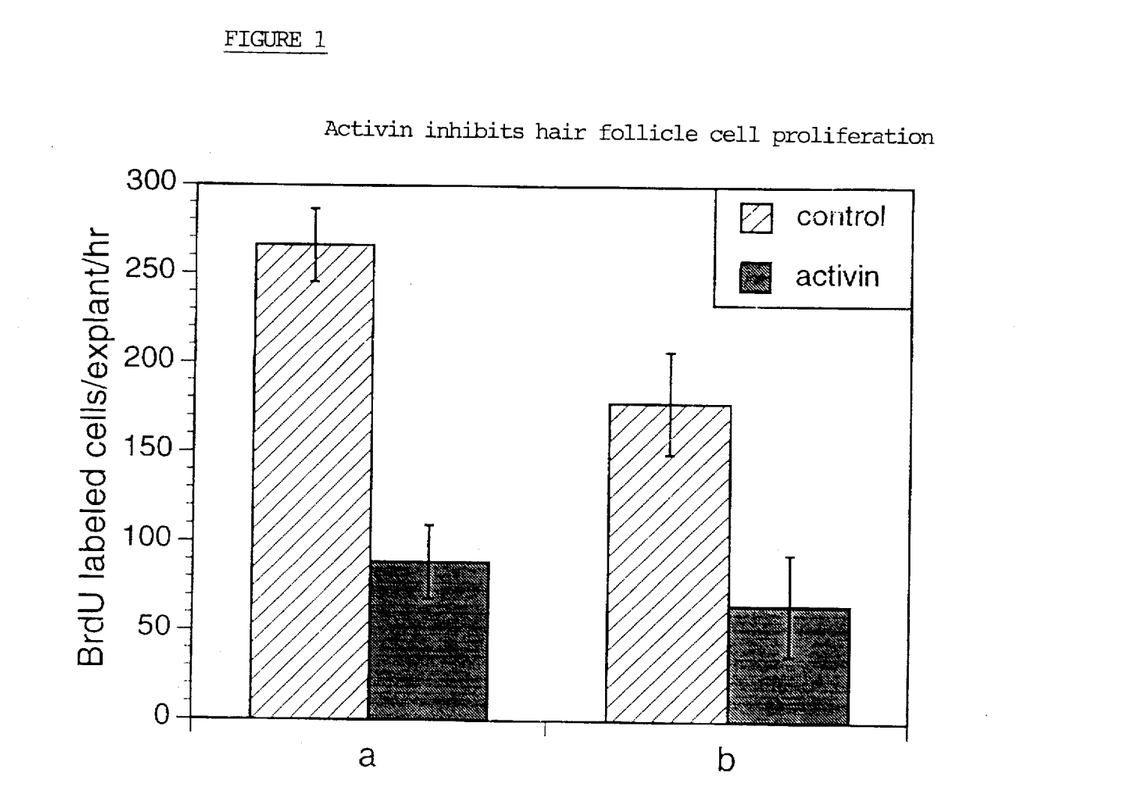
FIG. 1 is a diagram illustrating the effect of recombinant human activin A on proliferation of hair follicle cells from guinea pig skin explants. A and B represent two independent experiments in which at least 80 skin explants were examined per experiment.

Fresh skin was obtained by surgery from humans, mice and guinea pigs, cleaned from underlying fat tissue and cut into small explants. These explants were placed in a 24-well microculture plate in 400 µl of DMEM in the absence of serum under 5% $CO_2$ at 37° C., under constant shaking at 12× rpm, and incubated for 2 days. BrdU was added 3 hrs. before termination of incubation. Cells were fixed in 4% formaldehyde and stained with goat anti-brdU antibodies followed by anti-goat-FITC labeled IgG. Intact hair follicles that were present in vivo in their normal surroundings could be maintained under precisely controlled culture conditions, without the need of add serum or any other exogenous factor. Hair follicle cells in these explants were found to proliferate vigorously for several days under the conditions of the present method as indicated by the observation of a large number of hair follicle cells that incorporated BrdU. However, addition of preparations of recombinant human activin A to the hair follicle cultures resulted in a significant inhibition of hair follicle cell proliferation as detected by a decrease in BrdU incorporation. As shown in FIG. 1, addition of activin A to the explant (50 ng/ml) resulted in approximately 60–65% inhibition of hair follicle cell proliferation.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for reducing mammalian hair growth, comprising selecting an area of mammalian skin for which a reduced rate of hair growth is desired; and applying a composition including an amount of an activin A or a biologically active fragment thereof, wherein said fragment is functional in the inhibition of hair follicle cell proliferation, effective for inhibiting proliferation of hair follicle cells to cause a reduction in the rate of hair growth in said area of mammalian skin.

2. The method according to claim 1, which method is used to treat trichosis.

3. The method according to claim 1, which method is used to prolong depilation.

4. The method according to claim 2, which method is used to protect hair follicle cells from cell death caused by a cytotoxic agent which requires progression into S phase of the cell cycle for efficacy.

5. The method according to claim 4, wherein said cytotoxic agent is radiation treatment.

6. The method according to claim 1, wherein said activin A or biologically active fragment thereof is a native activin A.

7. The method according to claim 1, wherein said composition of activin A or biologically active fragment thereof is a cosmetic composition.

8. A method for inhibiting proliferation of hair follicle cells, which method comprises administering to a subject a pharmaceutical preparation including, as an active ingredient, an activin A or biologically active fragment thereof, wherein said fragment is functional in the inhibition of hair follicle cell proliferation, in an amount effective for inhibiting proliferation of hair follicle cells.

9. The method according to claim 8, wherein said activin A or biologically active fragment thereof is a native activin A.

10. The method according to claim 9, wherein said activin A or biologically active fragment thereof is human activin A.

11. The method according to claim 8, wherein said pharmaceutical preparation is administered to said subject by topical application.

12. The method according to claim 8, wherein said subject is a human subject.

13. The method according to claim 6, wherein said activin A or biologically active fragment thereof is human activin A.

14. The method according to claim 1, wherein said mammalian skin is human skin.

15. The method according to claim 1, wherein said composition is applied by topical application.

* * * * *